United States Patent
Bealka et al.

(10) Patent No.: US 6,586,675 B1
(45) Date of Patent: Jul. 1, 2003

(54) FEEDTHROUGH DEVICES

(75) Inventors: David Joseph Bealka, East Freetown, MA (US); Pedro Henrique Da Costa, New Bedford, MA (US)

(73) Assignee: Morgan Advanced Ceramics, Inc., Belmont, CA (US)

( * ) Notice: Subject to any disclaimer, the term of this patent is extended or adjusted under 35 U.S.C. 154(b) by 0 days.

(21) Appl. No.: 09/557,336

(22) Filed: Apr. 24, 2000

Related U.S. Application Data

(60) Provisional application No. 60/168,937, filed on Dec. 3, 1999.

(51) Int. Cl.$^7$ .................................................. H01J 5/00
(52) U.S. Cl. ............................... 174/50.56; 174/50.56; 607/36
(58) Field of Search ............................ 174/50.56, 50.5, 174/50.6, 50.7, 50.51, 50.52, 50.53, 50.54, 50.55; 607/36; 228/262.1, 262.61; 257/267; 29/862

(56) References Cited

U.S. PATENT DOCUMENTS

| | | | | |
|---|---|---|---|---|
| 4,180,700 A | | 12/1979 | Kraska et al. ....... 174/152 GM |
| 4,835,365 A | * | 5/1989 | Etheridge ................. 200/61.52 |
| 4,940,858 A | | 7/1990 | Taylor et al. ........ 174/152 GM |
| 4,991,582 A | | 2/1991 | Byers et al. ............. 128/419 P |
| 5,023,147 A | * | 6/1991 | Nakata et al. ............... 428/627 |
| 5,046,242 A | * | 9/1991 | Kuzma ................ 174/152 GM |
| 5,368,220 A | | 11/1994 | Mizuhara et al. ......... 228/124.5 |
| 5,440,447 A | | 8/1995 | Shipman et al. ............. 361/302 |
| 5,538,810 A | * | 7/1996 | Kaun .......................... 429/129 |
| 5,650,759 A | | 7/1997 | Hittman et al. ................ 33/182 |
| 5,681,172 A | * | 10/1997 | Moldenhauer ............... 439/95 |
| 5,700,724 A | * | 12/1997 | Shipe .......................... 257/698 |
| 5,750,926 A | | 5/1998 | Schulman et al. .......... 174/52.3 |
| 5,817,984 A | | 10/1998 | Taylor et al. ........ 174/152 GM |
| 5,825,608 A | | 10/1998 | Duva et al. .................. 361/302 |
| 5,833,714 A | * | 11/1998 | Loeb ........................... 607/137 |
| 5,866,851 A | | 2/1999 | Taylor et al. ........ 174/152 GM |
| 5,896,267 A | | 4/1999 | Hittman et al. ............. 361/302 |
| 5,905,627 A | | 5/1999 | Brendel et al. ............. 361/302 |

FOREIGN PATENT DOCUMENTS

| | | | |
|---|---|---|---|
| DE | 3434086 | 3/1986 | .................. 174/51 |

* cited by examiner

*Primary Examiner*—Dean A. Reichard
*Assistant Examiner*—Anton Harris
(74) *Attorney, Agent, or Firm*—Kilpatrick Stockton LLP; Dean W. Russell; Kristin D. Mallatt

(57) ABSTRACT

A feedthrough device having a ground wire that is coupled to both a metallic ferrule and to an insulating material and methods of making the device are provided. The ground wire is coupled or brazed between, adjacent to, or otherwise in direct contact with the metallic ferrule and the insulating material, for example, in a gap between the insulating material and the ferrule, or directly to the side of the insulating material and abutting the surface of the ferrule. If the ground wire is coupled or brazed in a gap, the gap may be formed by a notch in either the insulating material, the ferrule or both.

30 Claims, 6 Drawing Sheets

FEEDTHROUGH DEVICES

This application claims priority to U.S. Provisional No. 60/168,937, filed on Dec. 3, 1999, entitled "Feedthrough Devices," the entire contents of which are hereby incorporated herein by reference.

FIELD OF THE INVENTION

This invention is directed to feedthrough devices having grounded leads. In particular, the invention relates m to feedthrough devices with grounded leads that are suitable for use in medical implant devices or implantable pulse generators, such as pacemakers.

BACKGROUND OF THE INVENTION

It is desirable that feedthrough devices for such uses be of reduced size while maintaining a hermetic seal. There are numerous applications where it is desirable to carry electrical signals through a metal casing and to ground the electronic devices inside to the metal casing using ceramic-to-metal or glass-to-metal seals. For certain electrical devices, especially those for use in a living body, it is necessary to pass a wire into the housing of the device while maintaining a hermetic seal. For example, pacemakers designed for implantation in a living body require an opening in the housing of the device in order to pass conductive wires to the internal electric components. Because there is an absolute need to prevent body fluids from entering the interior of the device, the pass-through opening in the housing must be sealed in a gas-tight and liquid-tight manner.

In many instances, the size of the feed-through must be minimized due to constraints on the size of the completed device. This is particularly applicable, but not limited to the situations encountered in implantable devices such as cardiac pacemakers, cardiac defibrillators, cochlear implants, implantable hearing devices, and the like. Feed-through devices and the leads attached thereto must be robust enough to withstand manufacturing processes and the usage of the devices, and at the same time be made economically. The size of the feedthrough device limits how small an implantable device can be, because the width of a pacemaker or defibrillator case must be, at minimum, slightly larger than the width of the feedthrough.

Conventional feedthrough devices typically include a metallic ferrule, an insulating material, and at least one wire lead. If the feedthrough is used in a medical implant, the materials used should be biocompatible and resistant to corrosion, because the feedthrough becomes part of a case that protects the electronics inside the body.

More particularly, feedthrough devices have been employed in implantable devices, as disclosed and described in U.S. Pat. Nos. 5,905,627; 5,896,267; 5,825,608; 5,650,759; 4,940,858; and 5,866,851 as examples, which are hereby incorporated herein by reference. Typically, feedthrough devices include a metallic ferrule, which may have one or more flanges formed therein to facilitate mounting the device to the implantable medical device. The ferrule also has one or more openings through which a lead wire (or wires) may extend. Each lead wire is encapsulated and hermetically sealed within an insulating material that fills the remainder of the opening in the ferrule. The insulating material is bonded to both the lead wire and ferrule by glass sealing or brazing. The coupling of the above components must be done in such a way as to maintain a hermetic seal between each lead wire and the insulating material, and between the insulating material and the ferrule.

Some of the current practices employed for grounding electronic devices to a case in these feedthrough assemblies involve steps that use unnecessary space, are inefficient, and may cause yield problems. For example, one current practice includes attaching a lead directly to the case of the device, either by brazing or welding. However, in many instances, it is desirable for a lead to be grounded to the feedthrough upon delivery to an upper level assembly manufacturer. By having the ground wire in place prior to being delivered to an upper level assembly manufacturer, the upper level manufacturer is able to test the feedthrough device and any potentially attached electronics, rather than jeopardize the entire upper level assembly or case to which the device would be attached.

Current practice also involves welding a ground wire directly to a ferrule, away from the insulating material. Welding, however, is more labor intensive and expensive than brazing. A brazed joint is typically sturdier than a welded joint as well. Additionally, either brazing or welding the ground wire directly to the ferrule takes up a significant amount of space on the ferrule, because such a procedure requires an additional braze or weld joint. It also makes orienting the lead more difficult, because there is nothing supporting the sides of the ground wire. This additional braze joint must also be spatially separated from the original braze joints (those associated with the insulating material to metallic ferrule joints securing the wire lead) because the ground wire/ferrule braze joint can exert stress on the original braze joints, thus weakening both joints.

Additionally, brazing a ground wire into a separate opening on the ferrule also requires a separate braze load to be placed at the ground wire/ferrule interface. See, for to example, U.S. Pat. No. 5,905,627 issued to Brendel et al. Passing a ground wire through the ferrule in this manner, thus requiring an additional braze joint to be made, may adversely affect yields. As stated, a high integrity hermetic seal for medical implant devices is critical in order to prevent body fluids from penetrating the implanted device. Additionally, if the ground wire is to be placed in a thin area of the ferrule due to space constraints, assembly is more difficult because of the fixtures that would be required to hold the lead in position.

Furthermore, welding a ground wire to the ferrule after assembly of the feedthrough is also labor intensive and not as reliable. Welding a ground wire to the ferrule followed by brazing is more reliable but still labor intensive. This again requires a significant amount of space on the ferrule due to the additional braze joint that is necessary. In addition, this arrangement will not allow the ground wire to pass through the ferrule, which may be necessary for some implant devices.

In the special case in which a grounded lead must pass through the insulating material, present technology includes welding the ground wire to the ferrule or medical device case after assembly. For example, in the instance where a ground wire must pass through insulating material to ease attachment of a capacitor, it may be preferable to test the feedthrough/capacitor prior to welding the feedthrough assembly into the case that protects the electronics inside the body, as described above. This testing is impractical when the ground wire is welded to the case. If the ground wire is welded separately to the ferrule, the device requires more space.

There is also an industry practice of grounding a lead that is brazed to a ceramic. This involves laying a metallization layer or conductive member between the ferrule and the ground wire, across the surface of the ceramic, prior to brazing. The use of this procedure can cause yield problems due to braze flow between the ferrule and the ground wire, as capillary action may cause braze material to wick between the distinct braze joints, causing one or the other joint to have too much or too little braze.

Accordingly, there is a need in the art for a feedthrough device having a ground wire electrically coupled to the ferrule and located at an interface or opening of the ferrule and the insulating material. This has the advantages of minimizing the total space required for the device, providing efficient assembly, and minimizing the number of separate braze joints, thus improving the yield of the device while providing a reliable hermetic seal.

SUMMARY OF THE INVENTION

The present invention relates to a feedthrough device comprising a metallic ferrule, an insulating material, and a ground wire that is coupled to both the metallic ferrule and to the insulating material. The ground wire is preferably brazed to the metallic ferrule and to the insulating material, creating a single braze joint. The invention also relates to methods of coupling the ground wire to the ferrule and insulating material, and to medical devices containing the feedthrough device.

A feedthrough device according to one embodiment of the present invention has a metallic ferrule with an opening of sufficient size and shape to accommodate a lead wire and an insulating material; an insulating material disposed in the opening in the metallic ferrule, adapted to accommodate a lead wire and to support the lead wire in a nonconductive relation to the metallic ferrule; and a ground wire that is coupled, for example, by brazing, to the metallic ferrule and to the insulating material. The ground wire may be brazed in a gap between the insulating material and the ferrule, the ground wire being in contact with both the metallic ferrule and the insulating material. The gap may be formed by a notch in the insulating material, the metallic ferrule, or both. In another embodiment, the ground wire may be brazed directly to the surface of an insulating material and abut the surface of the ferrule, remaining in contact with both the metallic ferrule and insulating material.

The present invention also relates to methods of making a feedthrough device, comprising coupling a ground wire to a metallic ferrule and to an insulating material. More specifically, the invention relates to a method of coupling a ground wire to a feedthrough device comprising optionally metallizing a ceramic insulator if necessary, electrically isolating a wire lead within the ceramic insulator, positioning the metallized ceramic insulator and the lead wire within an opening in a metallic ferrule, positioning at least a portion of a ground wire between, adjacent to, or otherwise in direct contact with the metallized ceramic insulator and the metallic ferrule, and brazing all components together. The brazing step may be performed simultaneously. For example, once the components of the device have been assembled and the brazing material is put in place, the device may be placed in a furnace at appropriate brazing temperatures in order to melt the brazing material.

The invention also relates to a medical implant device comprising the above-described feedthrough device. The medical implant device comprises a housing and a feedthrough device coupled to the housing. The feedthrough device forms a hermetic seal with the housing while allowing the lead wire to pass into the housing.

One advantage of this invention is that it does not require an additional braze seal to secure the ground wire in position, since there is a single braze joint between the ground wire, the ferrule, and the insulating material. Furthermore, brazing the ground wire in a gap between the ferrule and the insulating material holds the lead in place more securely.

A further advantage of this invention is that less space is taken up on the feedthrough device. Another advantage of this invention is that it may be practiced using the same ferrule or insulator outline that may currently be in use. In other words, this invention potentially eliminates the need to retool ferrules or insulators, reducing costs to implement and to practice the invention.

Other features and advantages of the present invention will become apparent from the following detailed description in conjunction with the accompanying drawings, which illustrate, by way of example only, features of the present invention and are not intended to limit the invention in any way.

DETAILED DESCRIPTION

Figure 1A:
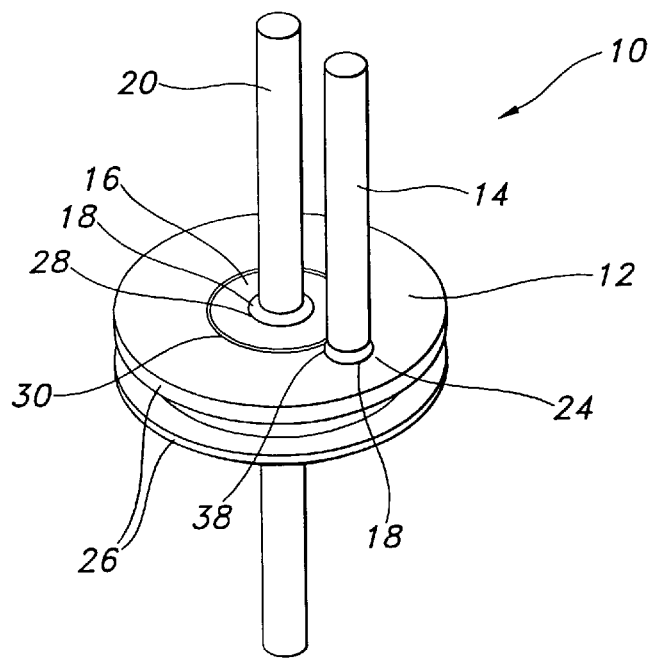
FIG. 1A is a perspective view of a feedthrough device of one embodiment of the present invention.
Figure 1B:
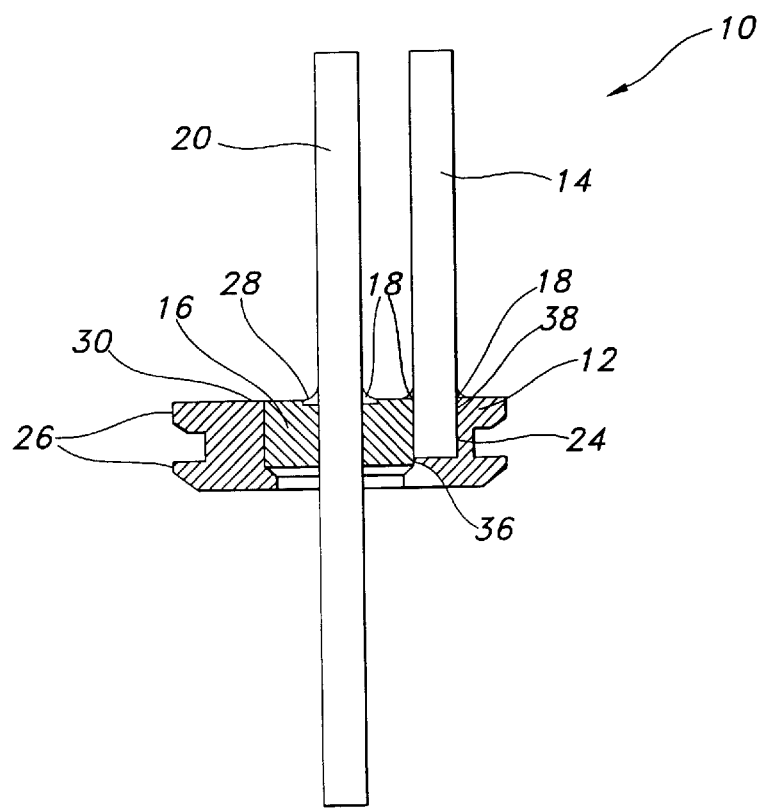
FIG. 1B is an elevation view partially cut-away of the feedthrough device of FIG. 1A.
Figure 2A:
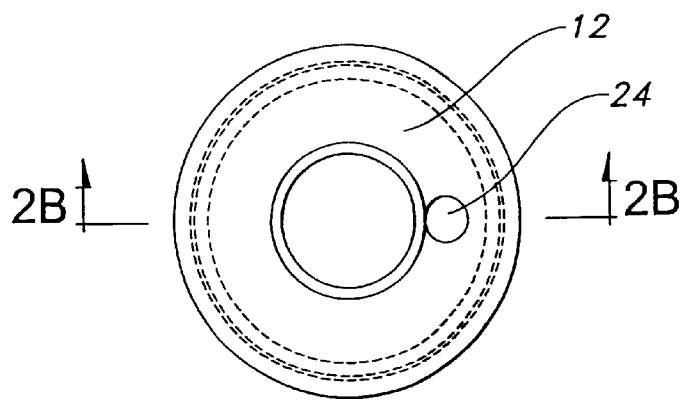
FIG. 2A is a top plan view of the ferrule having a notch of FIGS. 1A and 1B.
Figure 2B:
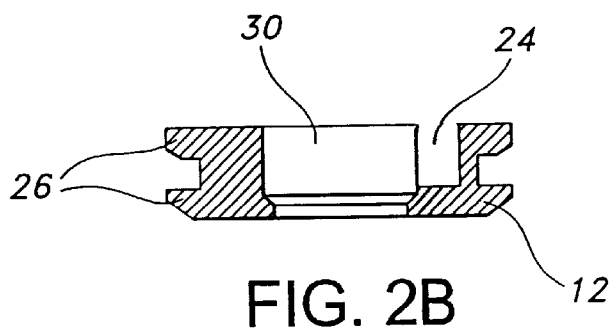
FIG. 2B is an elevation view partially cut-away of the ferrule of FIG. 2A.

Feedthrough device 10 shown in FIGS. 1A and 1B comprises metallic ferrule 12, ground wire 14, insulating material 16, brazing material 18, and wire lead 20. Feedthrough device 10 is shown as a single lead feedthrough device in this and the following figures. However, feedthrough devices according to the present invention may include multiple lead assemblies, which may have any number of leads, and are easily produced with two, three, four, five, or six leads. Ferrule 12 has an opening 30 from which lead wire 20 and insulating material 16 extend. Ferrule 12 is shown having two flanges 26 but may have any number of flanges that facilitate mounting device 10 to an implantable medical device, in particular, to its casing. Flanges 26 may be of any shape, non-limiting examples including rectangular, circular, or oblong. Ferrule 12 may be formed of any suitable material, non-limiting examples of which include titanium, niobium, tantalum, stainless steel, or combinations or alloys thereof.

Associated with ferrule 12 and separated therefrom by insulating material 16 is lead wire 20. Lead wire 20 may be formed of any suitable conductive material, non-limiting examples which include niobium, platinum, platinum/iridium, titanium, tantalum, tungsten, molybdenum and combinations or alloys thereof. At least a portion of lead wire 20 is encapsulated by insulating material 16, the insulating material having an opening 28 through which lead wire 20 passes. Lead wire 20 and insulating material 16 both extend through opening 30 in ferrule 12. The diameter of insulating material 16 fills the remainder of opening 30.

Insulating material 16 may be formed of any suitable insulating material. One type of suitable material a ceramic, non-limiting examples of which include alumina, zirconia, glass, or combinations thereof. If insulating-material 16 is formed from ceramic material, it preferably first has a metallic coating 36 (shown in FIG. 1B) applied to form a result conventionally called "metallization." After appropriate positioning of ground wire 14, as will be described in greater detail below, insulating material 16, lead wire 20, ground wire 14, and ferrule 12 are secured together and preferably brazed using brazing material 18 to form a hermetic seal at braze joint 38. Some examples of suitable brazing materials include gold, copper, silver, or alloys thereof. Of the plurality of braze joints formed, of particular importance is braze joint 38, the braze joint securing the ground wire 14 to the ferrule 12 and to the insulating material 16. If insulating material 16 is a glass, metal-to-glass seals (not shown) are formed at the perimeters of openings 28 and 30, and metallic coating 36 is not required.

As best seen in FIGS. 1A, 1B, 2A, and 2B, ferrule 12 has an optional indentation or notch 24 at or near opening 30, that helps to place ground wire 14 in contact with both ferrule 12 and insulating material 16. Ground wire 14 is razed in the interface or the opening between notch 24 of ferrule 12 and insulating material 16. Brazing ground wire 14 between ferrule 12 and insulating material 16 in this manner helps to keep ground wire 14 in the correct orientation because it is "lodged" between ferrule 12 and insulating material 16 due to its physical restraint by notch 24. The brazed surface area of ground wire 14 is greater than it would be if lead wire 14 were directly brazed to ferrule 12 without also being in contact with insulating material 16. This enables ground wire 14 to be held in place more securely and uses only one braze joint 38. This embodiment provides added support for ground wire 14 because of its positioning in notch 24. Braze joint 38 is the same joint for the insulating material 16 to ferrule 12 seal as the braze joint for sealing ground wire 14 to insulating material 16 and to ferrule 12.

Figure 3A:
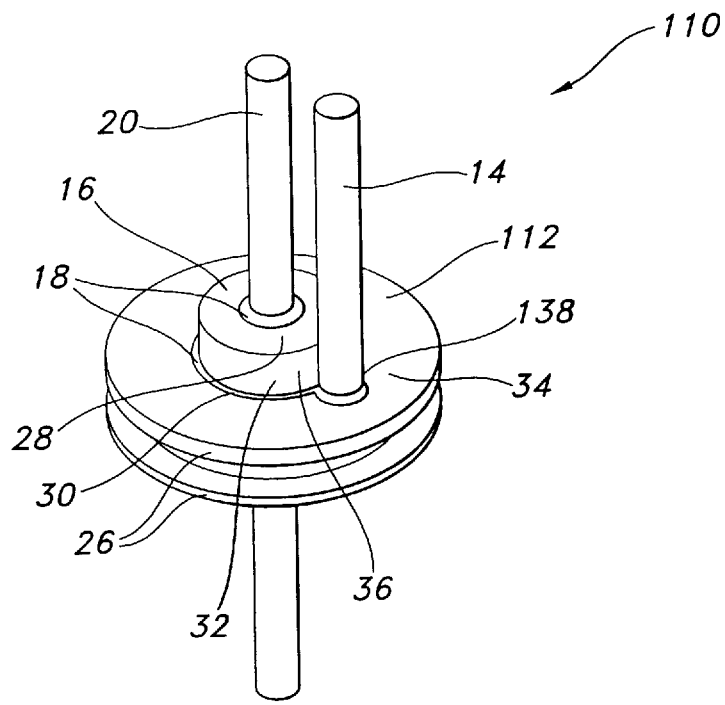
FIG. 3A is a perspective view of a feedthrough device of a second embodiment of the present invention.
Figure 3B:
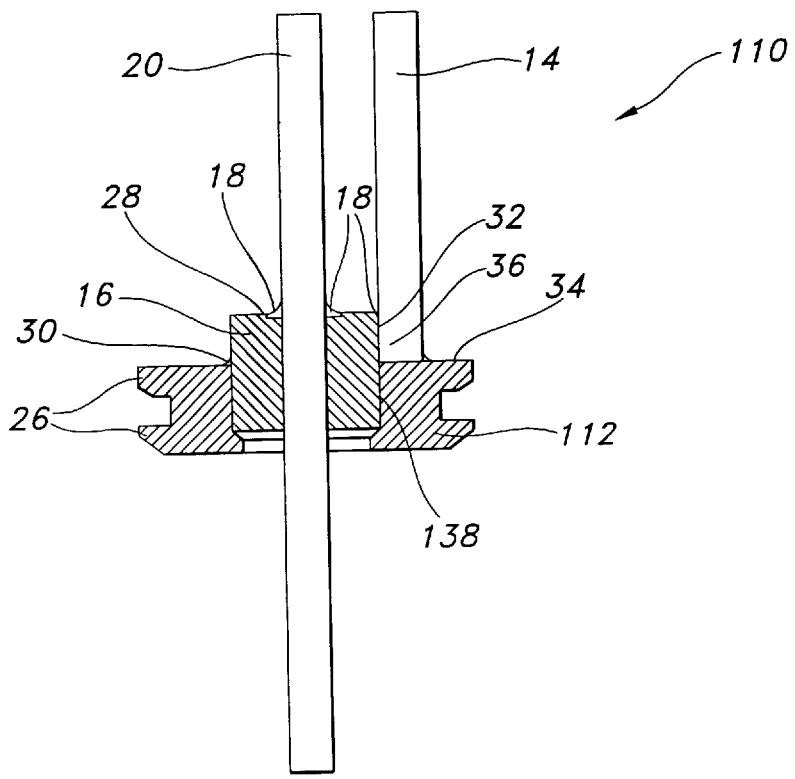
FIG. 3B is an elevation view partially cut-away of the feedthrough device of FIG. 3A.

While FIGS. 1A and 1B illustrate braze joint 38 located in notch 24 of ferrule 24, FIGS. 3A and 3B illustrate a feedthrough device 110 according to a second embodiment of the present invention with ground wire 14 brazed directly to a metallization 36 on outer surface 32 of insulating material 16 and to surface 34 of ferrule 112. Braze joint 138 extends from substantially flat, unnotched surface 34 of ferrule 112, to the upper portion of outer surface 32 of insulating material 16. While device 110 does not feature ground wire 14 brazed in a notch 24 of ferrule 12 or a notch in insulating material 16 (such as notch 22 described in more detail with reference to FIGS. 4A and 4B of feedthrough device 210 according to a third embodiment), feedthrough device 110 still saves space in the implant by requiring only one braze joint 138. The braze joint 138 securing ground wire 14 to both insulating material 16 and ferrule 12 is one and the same.

The length of contact between ground wire 14 and insulating material 16 can be varied, so that ground wire 14 may contact insulating material surface 32 substantially along the entire length of lead 14 or have very minimal contact. The length of contact is not of importance; of importance is providing a braze joint 38 between insulating material 16, ferrule 12, and ground wire 14. FIGS. 3A and 3B also show a lead wire 20 disposed in the opening 28 of insulating material 16 and secured in place with brazing material 18. Ferrule 112 is also shown having flanges 26 and opening 30.

Figure 5A:
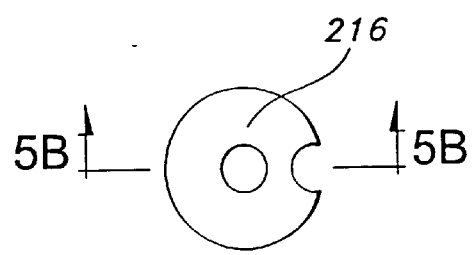
FIG. 5A is a top plan view of the insulating material having a notch of FIGS. 3A and 3B.
Figure 5B:
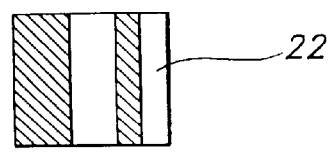
FIG. 5B is an elevation view partially cut-away of the insulating material having a notch of FIG. 5A.
Figure 4A:
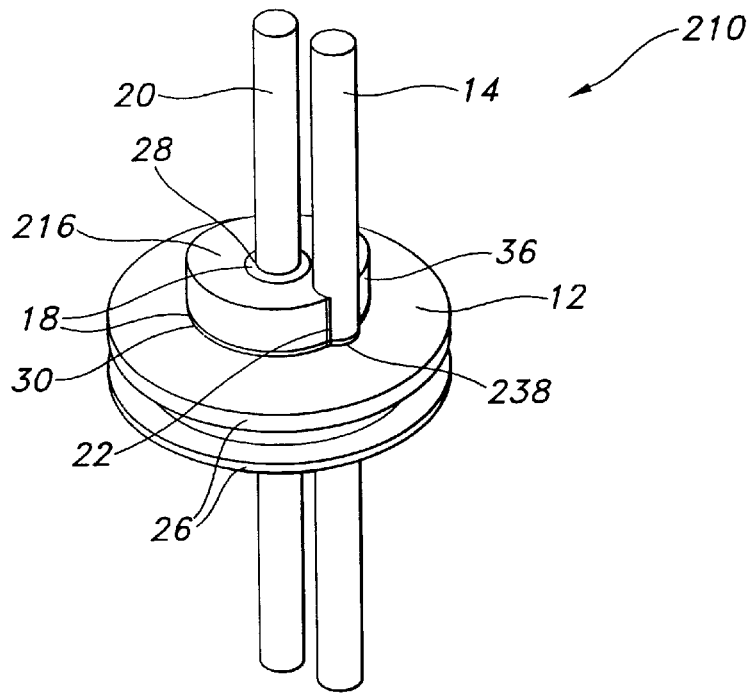
FIG. 4A is a perspective view of a feedthrough device of a third embodiment of the present invention.
Figure 4B:
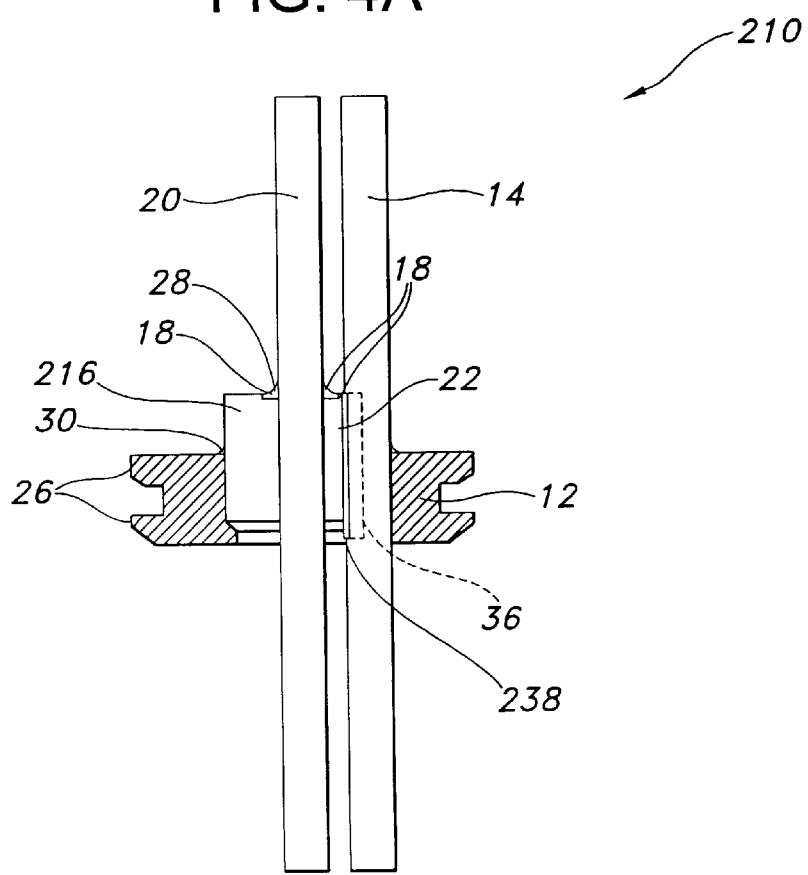
FIG. 4B is an elevation view partially cut-away of the feedthrough device of FIG. 4A.

FIGS. 4A and 4B illustrate a feedthrough device 210 according to a third embodiment of the invention, in which a ground wire 14 is brazed in notch 22 of insulating material 216. Notch 22 of insulating material 216 is more clearly depicted in FIGS. 5A and 5B. Device 210 obtains the same advantages as described above for FIGS. 1A and 1B, a difference being that ground wire 14 is brazed in notch 22 of insulating material 216, rather than in notch 24 of ferrule 12. Braze joint 238 is located substantially within notch 22 of insulating material 216. FIGS. 4A and 4B also show a lead wire 20 disposed in the opening 28 of insulating material 216 and secured in place with brazing material 18. Ferrule 12 is also shown having flanges 26 and opening 30. Insulating material 216 is also shown having metallized coating 36.

Figure 6A:
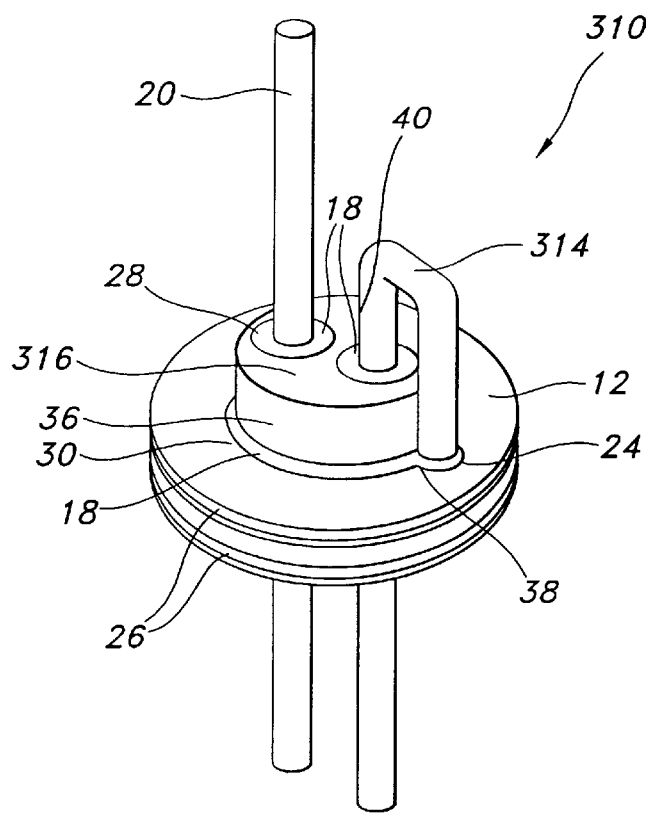
FIG. 6A is a perspective view of a feedthrough device of a fourth embodiment of the present invention.
Figure 6B:
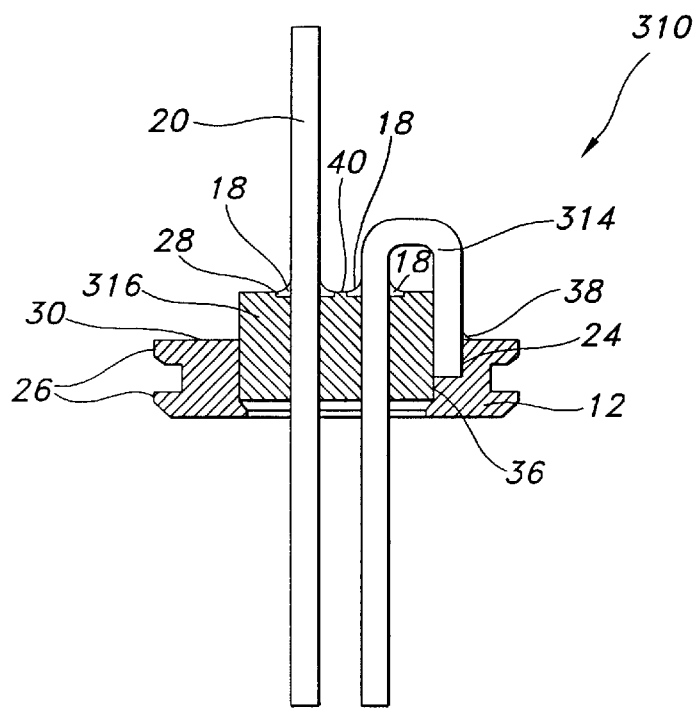
FIG. 6B is an elevation view partially cut-away of the feedthrough device of FIG. 6A.

Feedthrough devices of the present invention may also be associated with a capacitor. This coupling involves procedures that are known to one skilled in the art, for example those described by U.S. Pat. No. 5,440,447 issued to Shipman et al., the entire contents of which are hereby incorporated herein by reference. One embodiment of device 310 that may facilitate the grounding of a capacitor is shown in FIG. 6. In FIG. 6, ground wire 314 extends through the center of insulating material 316, through a second opening 40 in insulating material 316. Ground wire 314 extends through opening 40 and arches down to contact flange 12, where it is brazed with brazing material 18 to form braze joint 38. In this embodiment, flange 12 has notch 24, as depicted in FIGS. 1A, 1B, 2A, and 2B, or it may alternatively have substantially flat surface 34, as depicted in FIGS. 3A and 3B. FIGS. 6A and 6B also show a lead wire 20 disposed in the opening 28 of insulating material 316 and secured in place with brazing material 18. Ferrule 12 is also shown having flanges 26 and opening 30. Insulating material 316 is also shown having metallized coating 36.

The above-described figures illustrate several components common to all embodiments of the present invention. These include ferrule 12 and 112 shown in FIGS. 1–4, and 6; leads 14, 314, and 20 shown in FIGS. 1, 3–4, and 6; and insulating material 16, 216, 316 shown in FIGS. 1 and 3–6. The present invention may be practiced with these components having many different forms and being made of many different types of materials, depending on the desired device requirements. For example, either ferrule 12 or insulating material 16 or both may optionally have a notch on its surface, or neither may have a notch. Additionally, the materials and geometries described herein are merely exemplary, and are not meant to exclude additional variations from the scope of this invention.

Figure 7A:
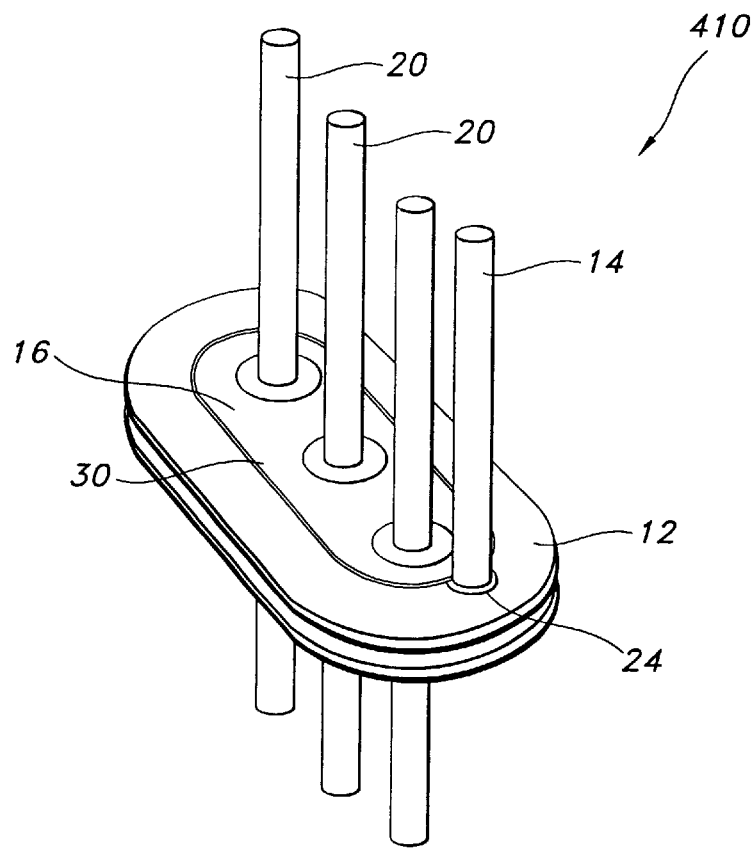
FIG. 7A is a perspective view of a feedthrough device having multiple leads according to a fifth embodiment of the present invention.
Figure 7B:
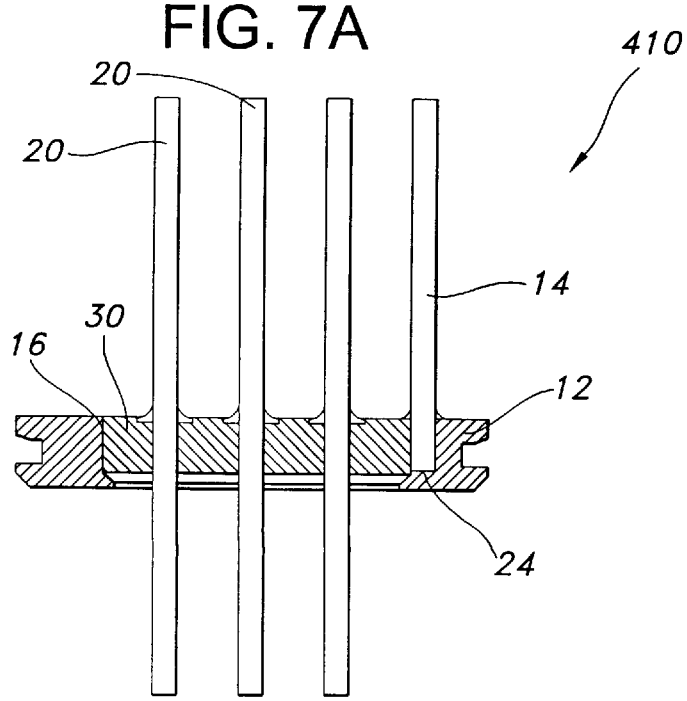
FIG. 7B is an elevation view partially cut-away of the feedthrough device of FIG. 7A.

A further embodiment of a feedthrough device 410 having a plurality of lead wires 20 is shown in FIGS. 7A and 7B.

The feedthrough device 410 includes a ferrule 12, a ground wire 14, insulating material 16, and a plurality of lead wires 20. The ferrule 12 has an opening 30 or a plurality of openings (not shown) for receiving the plurality of lead wires 20. The feedthrough device 410 also includes the insulating material 16 against which the ground wire 14 is brazed. The ferrule 12 includes the notch 24 for receiving a portion of the ground wire 14.

As described, a significant advantage of the present invention is that it saves valuable space on the feedthrough device. Because of the dramatic decrease in size in implantable medical devices, even saving a relatively small amount of space is extremely significant and beneficial. A further advantage of the present invention is that it minimizes the number of braze joints required to attach a ground wire to a feed through device, thus saving space and making manufacture more efficient.

The following describes a process used to make one embodiment of the invention in the case where the insulating material, ferrule, lead and ground pins, and brazing material are chosen for use in an implant application. The materials chosen should be biocompatible and corrosion resistant. For example, the components could include an alumina ceramic insulating material 16, titanium ferrule 12, platinum alloy pins 14, 20, and gold brazing material 18. Ceramic insulating material 16 is metallized with biocompatible metallic coating 36 or metallization that adheres to the surface of the insulating material where it is desirable to have braze material 18 bond metal members to insulating material 16. The electrically isolated lead wires, ground wires, and ferrule are placed in proper position relative to insulating material. More particularly, ground wire 14 is placed in contact with both the insulating material and the ferrule. The ferrule or the insulating material or both may have a notch, or neither may have a notch. If either or both the ferrule and the insulating material have a notch, the ground wire in placed within the gap formed between the ferrule and insulating material. The ground wire should be coupled to both the insulating material and the ferrule, whether or not it is "lodged" in a gap between the two components.

Brazing material 18, particularly braze preforms made of gold, are added to areas that require bonding. The assembly is then placed in a vacuum furnace and brazed at temperatures between about 600–1100° C. for alloys of gold, copper, or silver. More particularly, gold alloys may be brazed at a temperature between about 1050–1080° C., and even more particularly, near 1064° C., which is the melting point of pure gold, causing the gold braze material to flow and bond the structures together. Upon cooling from braze temperature, the ground wire will have been brazed in an interface or opening between insulating material and ferrule.

The feedthrough devices of the present invention may then be coupled to a capacitor using techniques known in the art. Additionally or alternatively, they may be associated with a medical implant device, including but not limited to a pacemaker, a defibrillator, a cochlear implant or hearing aid devices.

In summary, devices according to the invention allow a ground wire to be coupled in direct contact with an insulating material and a ferrule, using only one braze joint. More particularly, the ground wire is brazed at the interface formed between insulating material and ferrule. This enables the ground wire to be attached to a feedthrough device using less space, fewer steps, and less expense.

The particular embodiments of the invention having been described above are not limiting of the present invention, and those of skill in the art can readily determine that additional embodiments and features of the invention are within the scope of the appended claims and equivalents thereto.

What is claimed is:

1. A feedthrough device comprising:
   (a) a metallic ferrule;
   (b) an insulating material;
   (c) at least one electrically isolated lead wire within the insulating material; and
   (d) a ground wire coupled to the ferrule and to the insulating material in a single braze joint.

2. A feedthrough device comprising:
   (a) a metallic ferrule;
   (b) an insulating material; and
   (c) a ground wire coupled to the ferrule and to the insulating material, wherein the ground wire is brazed to the metallic ferrule and to the insulating material with brazing material, creating a single braze joint.

3. The feedthrough device of claim 1, wherein
   (a) the metallic ferrule comprises an opening therein of sufficient size and shape to accommodate a lead wire and an insulating material;
   (b) the insulating material is disposed in the opening in the metallic ferrule and is adapted to accommodate a lead wire and support a lead wire in a nonconductive relation to the metallic ferrule; and
   (c) the ground wire is coupled to the metallic ferrule and coupled to the insulating material by brazing.

4. The feedthrough device of claim 1, further comprising a lead wire passing through the opening in the metallic ferrule and supported therein by the insulating material.

5. The feedthrough device of claim 1, wherein the insulating material comprises a metallized surface and wherein the ground wire is brazed to the metallized surface.

6. A feedthrough device comprising:
   (a) a metallic ferrule;
   (b) an insulating material; and
   (c) a ground wire coupled to the ferrule and to the insulating material, wherein the metallic ferrule further comprises a surface having a notch therein, and wherein the ground wire is secured in the notch.

7. A feedthrough device comprising:
   (a) a metallic ferrule;
   (b) an insulating material; and
   (c) a ground wire coupled to the ferrule and to the insulating material, wherein the insulating material comprises a surface having a notch therein, and wherein the ground wire is secured in the notch.

8. A feedthrough device comprising:
   (a) a metallic ferrule;
   (b) an insulating material; and
   (c) a ground wire coupled to the ferrule and to the insulating material, wherein the insulating material comprises a surface having a notch therein, the metallic ferrule comprises a surface having a notch therein, and wherein the notches are aligned with the ground wire secured by brazing in the aligned notches.

9. The feedthrough device of claim 1, wherein the insulating material is selected from the group consisting of alumina, zirconia, glass, and combinations thereof.

10. The feedthrough device of claim 1, wherein the metallic ferrule comprises a material selected from the group consisting of titanium, niobium, tantalum, stainless steel, and alloys thereof.

11. The feedthrough device of claim 1, wherein the lead wire comprises a material selected from the group consisting of niobium, platinum, platinum/iridium, titanium, tantalum, tungsten, molybdenum and alloys thereof.

12. The feedthrough device of claim 2, wherein the brazing material is selected from the group consisting of gold, copper, silver, and alloys thereof.

13. The feedthrough device of claim 2, wherein (a) the metallic ferrule is comprised of titanium;

(b) the insulating material is comprised of alumina ceramic;

(b) the ground wire is comprised of platinum or a platinum alloy; and (d) the brazing material is comprised of gold.

14. A method of making the feedthrough device of claim 1, comprising coupling a ground wire to a metallic ferrule and to an insulating material.

15. The method of claim 14, further comprising:

(a) providing the metallic ferrule having an opening;

(a) disposing the insulating material in the opening in the metallic ferrule; and (b) coupling the ground wire to the insulating material and to the metallic ferrule by brazing.

16. The method of claim 14, wherein the coupling of the ground wire to the insulating material and to the metallic ferrule comprises brazing.

17. The method of claim 14, further comprising metallizing a surface of the insulating material and brazing the ground wire thereto.

18. The method of claim 15, wherein the insulating material has an opening to accommodate a lead wire and wherein a lead wire is disposed in the opening of the insulating material in nonconductive relation to the metallic ferrule.

19. A method of coupling a ground wire to a feedthrough device comprising:

(a) providing a ceramic insulating material;

(b) electrically isolating a lead wire within the insulating material;

(c) positioning the insulating material and the lead wire within an opening in a metallic ferrule;

(d) positioning at least a portion of a ground wire adjacent to the insulating material and adjacent to the metallic ferrule;

(e) brazing the ground wire to the insulating material and to the metallic ferrule in a singe braze joint;

(f) brazing the lead wire to the insulating material; and (g) brazing the insulating material to the metallic ferrule.

20. The method of claim 19, wherein the ceramic insulating material is metallized to form a metallized insulator.

21. A method of coupling a ground wire to a feedthrough device comprising:

(a) providing a ceramic insulating material;

(b) electrically isolating a lead wire within the insulating material;

(c) positioning the insulating material and the lead wire within an opening in a metallic ferrule;

(d) positioning at least a portion of a ground wire adjacent to the insulating material and adjacent to the metallic ferrule;

(e) brazing the ground wire to the insulating material and to the metallic ferrule;

(f) brazing the lead wire to the insulating material; and (g) brazing the insulating material to the metallic ferrule, wherein (e)–(g) are performed substantially simultaneously.

22. The method of claim 19, wherein the brazing is conducted at a temperature between about 600° C. and about 1100° C.

23. The method of claim 22, wherein the brazing is conducted at a temperature between about 1050° C. and about 1080° C.

24. The method of claim 23, wherein the brazing is conducted at a temperature of about 1064° C.

25. The method of claim 19, wherein (a) the ceramic insulating material is comprised of alumina ceramic;

(b) the metallic ferrule is comprised of titanium;

(c) the lead wire and ground wire are comprised of platinum or a platinum alloy; and (d) the brazing material is comprised of gold.

26. A medical implant device comprising a feedthrough comprising:

(a) a lead wire;

(b) a metallic ferrule comprising an opening therein of sufficient size and shape to accommodate the lead wire and an insulating material;

(c) an insulating material disposed in the opening in the metallic ferrule, adapted to accommodate the lead wire and support the lead wire in nonconductive relation to the metallic ferrule; and (d) a ground wire coupled to the metallic ferrule and coupled to the insulating material in a single braze joint.

27. The medical implant device of claim 26, wherein the medical implant device comprises a housing, and wherein the feedthrough is coupled to the housing, thereby forming a hermetic seal with the housing while allowing the lead wire to pass into the housing.

28. The medical implant device of claim 26, wherein the medical implant device comprises a cardiac pacemaker.

29. The medical implant device of claim 26, wherein the medical implant device comprises a cardiac defibrillator.

30. The medical implant device of claim 26, wherein the medical implant device comprises a cochlear implant or an implantable hearing device.

* * * * *